United States Patent [19]
Andrews et al.

[11] Patent Number: 5,460,833
[45] Date of Patent: Oct. 24, 1995

[54] DISINFECTANT COMPOSITION

[75] Inventors: Jeffrey F. Andrews, Stillwater; Janet F. Munson, Plymouth, both of Minn.

[73] Assignee: Minnesota Mining and Manufacturing Company, St. Paul, Minn.

[21] Appl. No.: 407,982

[22] Filed: Mar. 22, 1995

Related U.S. Application Data

[63] Continuation of Ser. No. 121,283, Sep. 14, 1993, abandoned.

[51] Int. Cl.$^6$ .......................... A01N 37/02; A01N 59/26; A23B 4/027; A23B 4/12
[52] U.S. Cl. .................. 424/606; 514/474; 514/546; 514/547; 514/549; 514/352; 514/557; 514/566; 514/570; 514/571; 514/574; 514/711; 514/772; 514/772.1; 514/772.3; 514/785; 424/78.08; 424/78.17; 424/78.31; 424/78.37; 426/321; 426/326; 426/331; 426/332; 426/335
[58] Field of Search ........................... 514/546, 549, 514/552, 557, 711, 474, 547, 566, 570, 571, 574, 772, 772.1, 772.3, 785; 426/321, 326, 335, 331; 422/28, 34; 424/606, 78.08, 78.17, 78.31, 78.37

[56] References Cited

U.S. PATENT DOCUMENTS

| | | | |
|---|---|---|---|
| 3,124,468 | 3/1964 | Williams | 99/174 |
| 3,806,615 | 4/1974 | Frankenfeld et al. | 426/328 |
| 4,002,775 | 1/1977 | Kabara | 426/532 |
| 4,067,997 | 1/1978 | Kabara | 424/312 |
| 4,160,820 | 7/1979 | Wagenknecht et al. | 424/48 |
| 4,189,481 | 2/1980 | Kabara | 424/248.54 |
| 4,299,852 | 11/1981 | Ueno et al. | 426/266 |
| 4,683,618 | 8/1987 | O'Brien | 17/51 |
| 4,722,941 | 2/1988 | Eckert et al. | 514/784 |
| 4,766,646 | 7/1988 | Parker | 17/51 |
| 4,770,884 | 9/1988 | Hill et al. | 426/332 |
| 4,849,237 | 7/1989 | Hurst | 426/332 |
| 5,069,922 | 12/1991 | Brotsky et al. | 426/332 |
| 5,093,140 | 3/1992 | Watanabe | 426/326 |
| 5,143,739 | 9/1992 | Bender et al. | 426/332 |
| 5,208,257 | 5/1993 | Kabara | 514/552 |
| 5,219,887 | 6/1993 | Andrews et al. | 514/552 |
| 5,380,756 | 1/1995 | Andrews et al. | 514/552 |

FOREIGN PATENT DOCUMENTS

| | | |
|---|---|---|
| 0243145 | 10/1987 | European Pat. Off. . |
| 0244144 | 11/1987 | European Pat. Off. . |
| 0312519 | 4/1989 | European Pat. Off. . |
| 0530861A2 | 3/1993 | European Pat. Off. . |
| WO92/21320 | 12/1992 | WIPO . |
| WO95/07616 | 3/1995 | WIPO . |

OTHER PUBLICATIONS

Manual of Clinical Microbiology, 3rd edition, Lennette, E. H. et al. (eds.), published 1980 by American Society for Microbiology, Washington D.C., p. 478.

Abstract, Derwent Publication, JP 76–84022, Sep. 22, 1976, abstracting JP51–106752 (1976).

Abstract, Derwent Publication, JP 77–22781, Feb. 17, 1977, abstracting JP52–21317 (1977).

Abstract, Derwent Publication, JP 77–73621, Sep. 3, 1977, abstracting JP52–105211 (1977).

CH 634 749 abstract, Feb. 28, 1983.

Baker et al., "Antimicrobial Properties of Lauricidin in Mechanically Deboned Chicken, Minced Fish and Chicken Sausage", *J. of Food Safety*, 4(1982), pp. 177–184.

Bell et al., "The Efficacy of Nisin, Sorbic Acid and Monolaurin as Preservatives in Pasteurized Cured Meat Products", *Food Microbiology*, 4, 1987, pp. 277–283.

Dychdala, "Acid–Anionic Surfactant Sanitizers", *Disinfection, Sterilization, and Preservation*, 2nd Edition, (16) pp. 319–323, 1977.

Cunningham, "Methods of Preservation of Poultry Products", *The Microbiology of Poultry Meat Products*, Chapter 9, 1987, pp. 275–292.

Hall et al., "Spice Extracts, Lauricidin, and Propylene Glycol as Inhibitors of *Clostridium botulinum* in Turkey Frankfurter Slurries", *Poultry Science*, vol. 65 (6), 1986, pp. 1167–1171.

Izat et al., "Effects of Lactic Acid in Processing Waters on the Incidence of Salmonellae on Broilers", *J. of Food Quality*, 13 (1990), pp. 295–306.

Izat et al., "Production and Processing Studies to Reduce the Incidence of Salmonella on Commercial Broilers", 1988.

Izat et al., "The Use of Propylene Glycol and/or Lactic Acid in Chill Water for Reducing Salmonellae on Broilers", *J. of Food Processing and Preservation*, 14 (1990), pp. 369–374.

Juven et al., "A Hot Acid Treatment for Eliminating Salmonella from Chicken Meat", *J. Milk Food Technol.*, vol. 37, No. 45 (1974), pp. 237–239.

Kabara, "GRAS Antimicrobial Agents for Cosmetic Products", *J. Soc. Cosmet. Chem.*, 31, 1–10 (1980).

Kabara, "Food–Grade Chemicals for Use in Designing Food Preservative Systems", *J. of Food Protection*, vol. 44, No. 8, (1981), pp. 633–647.

Kabara, "A New Preservative System for Food", *J. of Food Safety*, 4 (1982), pp. 13–25.

Kabara, "Medium–Chain Fatty Acids and Esters as Antimicrobial Agents", *Cosmetic and Drug Preservation*, (16), 1984, pp. 275–304.

(List continued on next page.)

Primary Examiner—Allen J. Robinson
Assistant Examiner—John D. Pak
Attorney, Agent, or Firm—Gary L. Griswold; Walter N. Kirn; Paul W. Busse

[57] ABSTRACT

The present invention is generally related to a product and a process to reduce the microbial contamination of processed meat and is particularly related to a product and a process to disinfect poultry carcasses using a disinfectant composition containing a fatty acid monoester, an acid or chelating agent, and a food grade surfactant. These components may be combined in either an aqueous or nonaqueous vehicle as desired. The present combination is effective against pathogenic and undesired bacteria. Advantageously, the present composition does not detrimentally alter the taste, texture, color, odor or appearance of the processed meat.

9 Claims, No Drawings

OTHER PUBLICATIONS

Kato et al., "Combined Effect of Different Drugs on the Antibacterial Activity of Fatty Acids and Their Esters", vol. 3, No. 8 (1975).

Kato et al., "Combined Effect of Citric and Polyphosphoric Acid on the Antibacterial Activity of Monoglycerides", vol. 4, No. 6 (1976).

Kotula et al., "Effect of Postchill Washing on Bacterial Counts of Broiler Chickens", *Poultry Science*, vol. 46, No. 5 (1967).

Nakagaki et al., "Solubility and Hydrolysis Rate of 1–Monolaurin in Aqueous Solutions", *Yakugaku Zasshi*, vol. 90 (10) 1970, pp. 1310–1315.

Steinhauer et al., "The Effect of Food Grade Polyphosphates on the Microbial Population of Chicken Meat", pp. 618–625, 1963.

Thomson et al., "Chlorine, Acid, and Heat Treatments to Eliminate Salmonella on Broiler Carcasses", *Poultry Science*, 55 (1976), pp. 1513–1517.

Thomson et al., "Control of Salmonella and Extention of Shelf–Life of Broiler Carcasses with a Glutaraldehyde Product", *J. of Food Science*, vol. 42, No. 5 (1977), pp. 1353–1355.

Thomson et al., "Minimizing Salmonella Contamination Broiler Carcasses with Poly (Hexamethylenebiguanide Hydrochloride)", *J. of Food Protection*, vol. 44, No. 6 (1981), pp. 440–441.

Press Conference Report, "Salmonella Reduction Process Receives Approval", *Food Technology*, 1993.

Wooley, "EDTA–tris Potentiation of Antimicrobial Agents", *Modern Veterinary Practice*, (1983), pp. 113–116.

5,460,833

DISINFECTANT COMPOSITION

This is a continuation of application Ser. No. 08/121,283 filed Sep. 14, 1993, now abandoned.

The present invention is generally related to a product and process to reduce the microbial contamination of processed meat and is particularly related to a product and process to disinfect poultry carcasses using a composition containing a fatty acid monoester, an acid and a surfactant.

BACKGROUND

Methods and processes to provide proper hygiene and microbial control are essential in modern meat processing plants. Current automated processing plants place increased demands on processing equipment and cleaning procedures to ensure that microbial control is maintained throughout the process in order to prevent contamination of large amounts of processed meat. In the poultry industry, bacterial control is particularly important because of the propensity of poultry to harbor pathogenic bacteria such as Salmonella spp., Enterobacter spp., Campylobacter spp. and Escherichia coli.

A typical poultry processing plant will generally be divided into two related processing stages. In the first stage, poultry processing steps include transporting, hanging, stunning, bleeding, scalding, defeathering and beheading. The bacterial load in this stage is generally high. Furthermore, the likelihood of cross contamination is very high during this stage because of the large numbers of bacteria brought into the process during slaughtering and defeathering. Common contact points of the poultry, such as scalding before defeathering, also present likely points of cross-contamination.

After the feathers and heads are removed, the poultry enters the second stage of the process which includes removing viscera, separating carcass and organs, washing, chilling, draining, packaging and shipping. Even though the bacterial loads in the second stage are typically not as high as in the first stage, this stage also requires careful bacterial control to ensure that no contamination or cross-contamination occurs in any of the processing steps and that the poultry is not contaminated when packaged and shipped.

A variety of materials and methods have been used to control bacterial contamination during poultry processing. For example, different antimicrobial agents or materials, including antibiotic compounds, have been used during the scalding and washing steps. At the present time, however, the use of antibiotic compounds to treat poultry is not approved by the Food and Drug Administration or U.S.D.A. and only sodium hypochlorite solutions, irradiation or trisodium phosphate solutions (See, e.g., U.S. Pat. Nos. 5,069,922 and 5,143,739 that report contacting defeathered and eviscerated poultry with a solution containing trisodium phosphate) are approved disinfectant treatments for poultry.

Alternative materials and processes, in addition to the approved treatments, have been reported. U.S. Pat. No. 5,093,140 reports adding a mixture of two or more lower molecular weight organic acids and a surfactant to the scalding or washing water. U.S. Pat. No. 4,849,237 reports sanitizing poultry carcasses with ozonated water. U.S. Pat. No. 4,770,884 reports contacting poultry carcasses with an acidic solution containing an anionic sulfate or sulphonate surfactant. U.S. Pat. No. 4,766,646 reports a method of disinfecting poultry carcasses by dipping the carcass in a solution containing acid polyformate salts.

Other known sanitizing agents or antibacterial materials include organic acids, hydrogen peroxide solutions, glutaraldehyde and other chemical or antibiotic compounds. See, e.g., Cunningham, Chapter 9—Methods of Preservation of Poultry Products, *The Microbiology of Poultry Meat Products*, Academic Press, 275–292 (1987). Testing of various organic acids indicate that concentrations of at least 2.0–5.0 wt. % are required. At these concentrations the organic acids are caustic and are not considered to be acceptable. More specifically, at these concentrations the organic acids cause severe discoloration to the skin and meat of the processed poultry.

The many different types of agents and materials that have been used to disinfect processed poultry clearly indicate that there is no generally accepted disinfectant agent or material for use on poultry. Essentially all of the agents or materials referred to above involve balancing desirable benefits against undesired effects. Specifically, any useful agent or material must have an effective antimicrobial activity against known pathogenic organisms but must not change or alter the texture, color, taste, odor or appearance of the poultry. In addition, the agent or material must be safe to use on a food product and should be easy to handle and use as well as being environmentally compatible and easy to dispose of or replace as needed. The stringent requirements needed to provide a suitable disinfecting product and process have prevented the acceptance of a generally recognized method for controlling or reducing bacterial contamination of processed poultry.

SUMMARY OF THE INVENTION

The present invention provides a processed meat disinfectant composition having effective antimicrobial activity without detrimentally affecting the taste, texture, color, odor or appearance of the processed meat, particularly poultry, and thus solves the problems associated with known agents identified above. This invention provides a poultry disinfectant composition containing i) a fatty acid monoester such as glycerol monoesters of lauric acid or propylene glycol monoesters of caprylic and capric acid, ii) an acid or chelating agent such as lactic acid, tartaric acid, adipic acid, succinic acid, citric acid, ascorbic acid, malic acid, mandelic acid, acetic acid, sorbic acid, sodium acid pyrophosphate, acidic sodium hexametaphosphate (SPORIX), or ethylenediaminetetraacetic acid and salts thereof, and iii) a food grade surfactant.

These three components may be combined in either an aqueous or nonaqueous vehicle as desired. The combination of the three components provides a composition that has effective antimicrobial activity when the three components are used together. If any of the three components are used alone, effective antimicrobial activity would not be possible except at concentrations which adversely affect the organoleptic characteristics of the poultry. When all three components are used together, however, the combination is effective against pathogenic and undesired bacteria.

Advantageously, the present composition does not change or alter the taste, texture, color, odor or appearance of the processed poultry and actually increases the shelf-life of the poultry compared to untreated poultry or poultry treated with chlorine solutions. Furthermore, the present composition does not pose any harmful toxicology or environmental problems. The composition is also readily handled at the processing plant and is compatible with current processing equipment.

In a preferred embodiment of the present invention, the fatty acid monoester is the glycerol monoester of lauric acid and/or the propylene glycol monoester of caprylic acid, the acid is acetic, lactic, tartaric, or mandelic acid and the food grade surfactant is dioctyl sodium sulfosuccinate or sodium lauryl sulfate. These three components may be used in a variety of vehicles such as water, propylene glycol and polyethylene glycol as well as mixtures of these vehicles. In many applications, water is a preferred vehicle.

In an alternative embodiment, the composition of the present invention also includes a nonionic surfactant such as polyoxyethylene/polyoxypropylene block copolymer. The presence of surfactants in the composition serves, in part, to allow the composition to penetrate otherwise inaccessible or hard to wet areas of a poultry carcass.

In addition to the disinfectant composition described above, the present invention also includes a process of disinfecting a poultry carcass that includes the step of contacting the carcass with the above listed composition. This process may include, for example, a separate dip after chilling or a wash before chilling. Alternatively, the present process may be used as a part of either the chilling process or as part of the scalding process. The flexibility to be used in these various processes and the ability to be effective at either cold or hot temperatures which are used in known poultry processing plants is particularly desirable.

DETAILED DESCRIPTION

The present invention includes both a product and process to reduce the microbial contamination of processed meat or poultry using a disinfectant composition containing effective amounts of a fatty acid monoester, an acid or chelating agent, and a food grade surfactant. These three components may to be combined to form either an aqueous or nonaqueous combination in which the combination is effective against undesired or pathogenic bacteria. When the composition includes an anionic surfactant, it is effective against both gram-negative and gram-positive bacteria but does not change or alter the taste, texture, color, odor or appearance of the poultry.

In the present invention the following terms have the following meanings.

Effective Amount(s) means that amounts of components in a composition, as a whole, provides an antimicrobial activity having a spectrum of sufficient breadth to kill essentially most pathogenic or undesired bacteria such as bacteria known to cause or associated with food poisoning in humans or related to or associated with food spoilage or reduce the number of such bacteria to an acceptable level. In the present composition, the concentrations or amounts of the components, when considered separately, do not kill pathogenic or undesired bacteria or reduce the number of such bacteria to an acceptable level. Thus, the components of the composition when used together provide a synergistic antimicrobial activity when compared to the same components used alone under the same conditions.

Those of ordinary skill in the art will readily determine when a composition of the present invention provides synergistic antimicrobial activity using assay and bacterial screening methods well known in the art. One readily performed assay involves exposing selected known or readily available viable bacterial strains, such as Escherichia coli, Staphylococcus spp., Streptococcus spp., Pseudomonas spp., or Salmonella spp., to a test composition at a predetermined bacterial burden level in a culture media at an appropriate temperature. After a sufficient contact time, an aliquot of a sample containing the exposed bacteria is collected, diluted, and plated out on agar. The plated sample of bacteria is incubated for about forty-eight hours and the number of viable bacterial colonies growing on the plate is counted. Once colonies have been counted the reduction in the number of bacteria caused by the test composition is readily determined. Bacterial reduction is generally reported as $\log_{10}$ reduction determined by the difference between the $\log_{10}$ of the initial inoculum count and the $\log_{10}$ of the inoculum count after exposure.

Shelf-Life means a period of time it takes for a processed food to spoil. For example, poultry is considered to be spoiled if the bacterial count for an area of skin (one square centimeter) is equal to or greater than $10^7$ C.F.U/cm² (colony forming units per square centimeter).

Fatty acid monoesters which may be used in the present composition include known glycerol monoesters of lauric, caprylic and capric acid and/or propylene glycol monoesters of lauric, caprylic or capric acid. These monoesters have been reported to be food grade, generally recognized as safe (GRAS) materials and have been reported to be effective as food preservatives and effective as topical pharmaceutical agents. For example, Kabara, *J. of Food Protection*, 44:633–647 (1981) and Kabara, *J. of Food Safety*, 4:13–25 (1982) report that LAURICIDIN (the glycerol monoester of lauric acid commonly referred to as monolaurin), a food grade phenolic and a chelating agent may be useful in designing food preservative systems. This report also indicates that the presence of acidulants enhances the microbial spectrum and activity of monolaurin. Bell et al., *Meat Ind. Res. Inst.*, 4:4 (1987) report that sorbic acid and monolaurin may be a useful luncheon meat preservatives. Ueno et al., U.S. Pat. No. 4,299,852 report that sorbic acid and monolaurin may be used in a process to prepare botulinal-resistant meat products.

The amounts of fatty acid monoesters in the present invention which are used to provide a concentrated composition are between about 1.0–50.0 wt. % and preferably about 1.0–20.0 wt. %. When used as a disinfectant, the concentrate is typically diluted with water to provide a fatty acid monoester concentration of between about 0.001–5.0 wt. % and preferably about 0.005–1.0 wt. %.

In this invention, acid or chelating agents which may be used are also generally food grade, GRAS materials. Preferred materials include lactic acid, tartaric acid, adipic acid, succinic acid, citric acid, ascorbic acid, malic acid, mandelic acid, acetic acid, sorbic acid, sodium acid pyrophosphate, acidic sodium hexametaphosphate (such as SPORIX acidic sodium hexametaphosphate), and ethylenediaminetetraacetic acid and salts thereof. These materials are typically components which have been used with glyceryl fatty acid esters to provide useful topical antimicrobial pharmaceutical compositions and preservative compositions. See, e.g., Kabara, EPO 0 243 145 published Oct. 28, 1987 and Karbara, EPO 0 244 144 published Nov. 4, 1987.

The amounts of acid or chelating agent in the present invention which are used to provide a concentrated composition are between about 1.0–20.0 wt. % and preferably about 1.0–10.0 wt. %. When used, the concentrate is typically diluted with water to provide an acid or chelating concentration of between about 0.01–1.0 wt. % and preferably about 0.01–0.5 wt. %. These concentrations of the acids or chelating agents, if used alone, do not provide effective antimicrobial activity and are present in the disinfectant composition at concentrations which are lower than have been previously used in other disinfectants. Lower concentrations of acid are necessary, in part, in order to avoid undesired changes or alterations to the taste, texture, color, odor or appearance of the poultry.

Suitable anionic surfactants as well as nonionic surfactants include dioctyl sodium sulfosuccinate, sodium lauryl sulfate and polyoxyalkylene derivatives of propylene glycol. Various surfactants are also reported in EPO 0 243 145 and EPO 0 244 144. Preferably, food grade and/or GRAS materials are used in amounts which provide a concentrated composition of between about 1.0–30.0 wt. % and preferably about 4.0–12.0 wt. %. When used, the concentrate is typically diluted with water to provide a surfactant concentration of between about 0.001–1.0 wt. % and preferably 0.01–0.5 wt. %.

A particularly preferred concentrated composition of the present invention is listed below.

| COMPONENT | WT. % |
|---|---|
| glycerol monolaurate<br>Lauricidin Inc.<br>Okemos, Mi | 1.0 |
| propylene glycol monocaprylate<br>Karlshamns<br>Columbus, OH | 2.5 |
| propylnen glycol monocaprate<br>Karlshamns<br>Columbus, OH | 2.5 |
| lactic acid<br>R.I.T.A. Corp.<br>Woodstock, IL | 6.0 |
| PLURONIC F-68 surfactant<br>BASF<br>Parsippany, NJ | 10.0 |
| propylene glycol<br>J.T. Baker, Inc.<br>Phillipsburg, NJ | 15.0 |
| dioctyl sodium sulfosuccinate (50 wt. %<br>in ethanol)<br>American Cyanamid<br>Wayne, NJ | 10.0 |
| deionized water | 53.0 |

The composition of the present invention may be prepared by combining the above described components using processes and procedures well known to those of ordinary skill in the art. Briefly, a concentrated composition is prepared by adding PLURONIC F-68 surfactant to cold deionized water and then adding the acid to the cold mixture to form a first solution. A second solution is prepared by adding glycerol monolaurate, propylene glycol monocaprylate and propylene glycol monocaprate to propylene glycol. Due to the solubility of dioctyl sodium sulfosuccinate, it may be added to either the first solution or to the second solution. The final composition is then prepared by heating the first solution to about 160° F. and heating the second solution to about 140° F. The heated solutions are then combined and allowed to cool to ambient temperature. When used as a poultry disinfectant composition, the concentrated composition is diluted with water. Typical dilution ratios are between about 16:1 to about 128:1.

The composition of the present invention may be used in a poultry processing plant in a variety of suitable ways during various stages of the process. For example, the present composition may be applied to the poultry as a spray, a rinse, or a wash solution. In addition, the present invention has a wide useful temperature range which allows the composition to be used at different stages in the process plant. For example, the composition may be used both in the scald tank as well as in the chill tank. In a preferred process, poultry carcasses are washed with the composition just before they are placed in the chill tank Other modes of treating poultry carcasses will be readily apparent to those of ordinary skill in the art after review of the present specification.

EXAMPLES

The following examples are intended to provide further details and embodiments related to the practice of the present invention. These examples are provided for illustrative purposes and should not be construed to limit the scope of the present invention which is defined in the appended claims.

The components and/or reagents listed in the examples are commercially available from the following sources: glycerol monolaurate (Lauricidin Inc., Okemos, MI), PLURONIC F-68 (BASF, Parisippany, N.J.), propylene glycol monolaurate, monocaprate, and monocaprylate (Karlshamms, Columbus, OH), SPORIX, acidic sodium hexametaphosphate (International Sourcing Inc., Upper Saddle River, N.J.), dioctyl sodium sulfosuccinate (American Cyanamid, Wayne, N.J.), sodium lauryl sulfate (Stepan Chemical Co., Northfield, Ill.), propylene glycol (J. T. Baker, Inc., Phillipsburg, N.J.), acetic acid, citric acid, mandelic acid, isopropanol (Mallinckrodt, Inc., Paris, Ky.), and lactic acid (R.I.T.A. Corp., Woodstock, Ill.).

Example 1—Antimicrobial Activity Testing

This example demonstrates that the three components of the present composition, when used together, provided effective antimicrobial activity but that the components, when used alone under similar conditions, did not provide adequate or effective antimicrobial activity.

The antimicrobial activity for the components tested alone are listed in Table 1. In Table 1, the antimicrobial activity is reported as a log reduction which is determined by calculating the difference between the $\log_{10}$ of the initial inoculum count and the $\log_{10}$ of the inoculum count after exposure to the listed components for either about two minutes or about ten minutes at about 25° C.

To determine bacterial kill-rate or $\log_{10}$ reduction, a 0.1 ml aliquot of a bacterial culture suspension incubated for about 24 hours in tryptic soy broth having an initial inoculum count of between about $10^6$–$10^8$ cells/ml was added to a test flask containing about 20 ml of a specific composition at about 25° C. In this example, culture suspensions were prepared from known cell lines E. coli, ATCC Number 25922 and S. aureus, ATCC Number 25923. After about two minutes, five minutes or ten minutes of this treatment, a 1.0 ml aliquot was taken from the test flask, diluted with about 9.0 ml letheen broth (letheen broth also neutralizes the microbial activity of the glycerol monoester of lauric acid) and then plated out on sheep blood agar plates using well known procedures. The inoculated plates were incubated at about 35° C. for forty-eight hours and then the colonies were counted and compared to the initial inoculum counts.

TABLE I

ANTIMICROBIAL ACTIVITY (LOG REDUCITONS) OF ONE COMPONENT

| COMPOSITION | S. AUREUS 2 MIN. | S. AUREUS 10 MIN. | E. COLI 2 MIN. | E. COLI 10 MIN. |
|---|---|---|---|---|
| GLYCERYL MONOLAURATE 1.0% PLURONIC F-68 10% | <2.96 | <2.96 | <2.71 | <2.71 |
| PROPYLENE GLYCOL MONOCAPRYLATE 1.0% PLURONIC F-68 10% | <3.10 | <3.10 | 3.92 | 4.16 |
| PROPYLENE GLYCOL MONOCAPRATE 1.0% PLURONIC F-68 10% | <3.10 | <3.10 | <2.55 | <2.55 |
| DIOCTYL SODIUM SULFOSUCCINATE (50% IN ETHANOL) | | | | |
| 0.10% | <2.41 | <2.41 | <2.65 | <2.65 |
| 0.50% | <2.94 | <2.94 | <2.30 | <2.30 |
| 2.50% | <2.84 | <2.94 | <2.30 | <2.30 |
| 5.00% | <2.52 | <2.52 | <2.27 | <2.27 |
| SODIUM LAURYL SULFATE | | | | |
| 0.10% | <2.63 | <2.63 | <2.33 | <2.33 |
| 1.00% | <2.63 | <2.63 | <2.33 | <2.33 |
| PLURONIC F-68 5.0% | <2.69 | <2.69 | <2.57 | <2.57 |
| PROPYLENE GLYCOL 15.0% | <2.59 | <2.59 | <2.59 | <2.59 |
| ACETIC ACID 1.0% | <2.96 | <2.96 | <2.71 | <2.71 |
| ASCORBIC ACID 1.0% | <2.91 | <2.91 | <2.40 | 3.35 |
| CITRIC ACID | | | | |
| 0.10% | <2.59 | <2.59 | <2.27 | <2.27 |
| 1.00% | <2.59 | <2.59 | <2.27 | 5.81 |
| LACTIC ACID | | | | |
| 0.10% | <2.59 | <2.59 | <2.59 | <2.59 |
| 1.00% DL MALIC ACID | <2.59 | <2.59 | <2.59 | 6.13 |
| 0.10% | <2.96 | <2.96 | <2.71 | <2.71 |
| 1.00% | <2.96 | <2.96 | <2.71 | <2.71 |
| DL MANDELIC ACID | | | | |
| 0.10% | <2.96 | <2.96 | <2.71 | <2.71 |
| 1.0% | 3.65 | >6.51 | 4.50 | >6.26 |
| SUCCINIC ACID | | | | |
| 0.10% | <2.84 | <2.84 | <2.30 | <2.30 |
| 1.00% | <2.84 | <2.84 | <2.30 | <2.30 |
| SPORIX | | | | |
| 0.1% | <2.94 | <2.94 | <2.63 | >6.18 |
| 1.0% | 3.44 | >6.48 | >6.18 | >6.19 |
| TARTARIC ACID | | | | |
| 0.10% | <2.33 | <2.33 | <2.15 | <2.15 |
| 1.00% | <2.33 | <2.33 | <2.15 | 5.34 |

The dam in Table 1 indicate that at low concentrations (less than about 1.0 wt. %) none of the components listed provided adequate or effective antimicrobial activity. Some of the organic acids listed in Table 1 provided some antimicrobial activity at higher concentrations (greater than about 1.0 wt. %) but the length of time needed for this activity (except for mandelic acid) was about ten minutes. In sum, none of the components tested separately were suitable for use as a poultry disinfectant composition.

The data in Table 2 also indicate that two component compositions including a fatty acid monoester and an anionic or a nonionic surfactant were not effective against gram-negative or gram-positive bacteria.

TABLE 2

ANTIMICROBIAL ACTIVITY (LOG REDUCTIONS) OF TWO COMPONENTS

| COMPOSITION | WT. % | S. AUREUS 2 MIN. | S. AUREUS 5 MIN. | S. AUREUS 10 MIN | E. COLI 2 MIN. | E. COLI 5 MIN | E. COLI 10 MIN. |
|---|---|---|---|---|---|---|---|
| PROPYLENE GLYCOL MONOCAPRYLATE | 1.0 | <2.10 | — | <3.10 | <2.55 | — | <2.55 |
| DOSS | 5.0 | | | | | | |
| WATER | 94.0 | | | | | | |
| PROPYLENE GLYCOL MONOCAPRATE | 1.0 | <3.10 | — | <3.10 | <2.55 | — | <2.55 |
| DOSS | 5.0 | | | | | | |
| WATER | 94.0 | | | | | | |
| PROPYLENE GLYCOL MONOLAURATE | 1.0 | <3.10 | — | <3.10 | <2.55 | — | <2.55 |
| DOSS | 5.0 | | | | | | |
| WATER | 94.0 | | | | | | |
| PROPYLENE GLYCOL MONOCAPRYLATE | 1.0 | <3.10 | <3.10 | <3.10 | 3.92 | 4.06 | 4.16 |
| PLURONIC F-68 | 5.0 | | | | | | |
| WATER | 94.0 | | | | | | |
| PROPYLENE GLYCOL MONOCAPRATE | 1.0 | <3.10 | <3.10 | <3.10 | <2.55 | <2.55 | <2.55 |
| PLURONIC F-68 | 5.0 | | | | | | |
| WATER | 94.0 | | | | | | |
| PROPYLENE GLYCOL MONOLAURATE | 1.0 | <3.10 | <3.10 | <3.10 | <2.55 | <2.55 | <2.55 |
| PLURONIC F-68 | 5.0 | | | | | | |
| WATER | 94.0 | | | | | | |
| GLYCEROL MONOLAURATE | 1.0 | <2.59 | <2.59 | <2.59 | <2.27 | <2.27 | <1.27 |

TABLE 2-continued

ANTIMICROBIAL ACTIVITY (LOG REDUCTIONS) OF TWO COMPONENTS

| | | S. AUREUS | | | E. COLI | | |
|---|---|---|---|---|---|---|---|
| COMPOSITION | WT. % | 2 MIN. | 5 MIN. | 10 MIN | 2 MIN. | 5 MIN | 10 MIN. |
| DOSS | 2.5 | | | | | | |
| WATER | 96.5 | | | | | | |

DOSS - dioctyl sodium sulfosuccinate (50 wt. % in ethanol)

Additional data listed in Table 3 indicate that the effective antimicrobial activity of a composition containing a fatty acid monoester, an organic acid and a food grade nonionic surfactant were effective against pathogenic or undesired bacteria typically associated with processed poultry including gram-negative bacteria such as Salmonella spp. and $E.$ $coli$. However, these compositions did not have any substantial activity against gram-positive bacteria such as $S.$ $aureus$.

anionic surfactant and a nonionic surfactant (with the exception that no nonionic surfactant is added when SPORIX acidic sodium hexametaphosphate is used) provided effective antimicrobial activity against both gram-negative and gram-positive bacteria when used at concentrations which were not detrimental to the taste, texture, color, odor or appearance of the processed poultry.

TABLE 3

ANTIMICROBIAL ACTIVITY (LOG REDUCTIONS) OF FATTY ACID MONOESTERS, ORGANIC ACIDS, AND NONIONIC SURFACTANT

| | | E. COLI | | | S. AUREUS | | |
|---|---|---|---|---|---|---|---|
| COMPOSITION | WT. % | 2 MIN. | 5 MIN. | 10 MIN. | 2 MIN. | 5 MIN. | 10 MIN. |
| PROPYLENE GLYCOL MONOCAPRYLATE | 0.5 | >5.65 | >5.65 | >5.65 | 2.94 | 4.39 | >6.24 |
| TARTARIC ACID | 0.1 | | | | | | |
| PLURONIC F-68 | 5.0 | | | | | | |
| WATER | 94.4 | | | | | | |
| PROPYLENE GLYCOL MONOCAPRATE | 0.5 | >5.65 | >5.65 | <2.70 | <2.70 | <2.70 | 3.26 |
| TARTARIC ACID | 0.1 | | | | | | |
| PLURONIC F-68 | 5.0 | | | | | | |
| WATER | 94.4 | | | | | | |
| PROPYLENE GLYCOL MONOLAURATE | 0.5 | 3.31 | 4.54 | 5.43 | <2.70 | <2.70 | <2.70 |
| TARTARIC ACID | 0.1 | | | | | | |
| PLURONIC F-68 | 5.0 | | | | | | |
| WATER | 94.4 | | | | | | |
| PROPYLENE GLYCOL MONOCAPRYLATE | 0.1 | >5.54 | >5.54 | >5.54 | <2.99 | <2.99 | <2.99 |
| LACTIC ACID | 0.1 | | | | | | |
| PLURONIC F-68 | 5.0 | | | | | | |
| WATER | 94.8 | | | | | | |
| PROPYLENE GLYCOL MONOCAPRATE | 0.1 | >5.54 | >5.54 | >S.54 | <2.99 | <2.99 | <2.99 |
| LACTIC ACID | 0.1 | | | | | | |
| PLURONIC F-68 | 5.0 | | | | | | |
| WATER | 94.8 | | | | | | |
| PROPYLENE GLYCOL MONOLAURATE | 0.1 | <1.99 | 4.17 | 5.28 | <2.99 | <2.99 | <2.99 |
| LACTIC ACID | 0.1 | | | | | | |
| PLURONIC F-68 | 5.0 | | | | | | |
| WATER | 94.8 | | | | | | |
| GLYCEROL MONOLAURATE | 0.50 | >5.89 | — | >5.89 | <2.99 | — | <2.89 |
| LACTIC ACID | 0.50 | | | | | | |
| PLURONIC F-68 | 5.00 | | | | | | |
| WATER | 94.00 | | | | | | |
| GLYCEROL MONOLAURATE | 0.50 | >5.89 | — | >5.89 | <2,89 | — | <2.89 |
| SUCCINIC ACID | 0.50 | | | | | | |
| PLURONIC-F-68 | 5.00 | | | | | | |
| WATER | 94.00 | | | | | | |
| GLYCEROL MONOLAURATE | 0.50 | 3.27 | — | 4.54 | <2.99 | — | <2.89 |
| CITRIC ACID | 0.50 | | | | | | |
| PLURONIC F-68 | 5.00 | | | | | | |
| WATER | 94.00 | | | | | | |
| GLYCEROL MONOLAURATE | 0.10 | <2.60 | — | >5.98 | <2.90 | — | <2.80 |
| ACETIC ACID | 0.10 | | | | | | |
| PLURONIC F-68 | 0.50 | | | | | | |
| WATER | 99.30 | | | | | | |

The data in Table 4 indicate that a disinfectant composition containing a fatty acid monoester, an organic acid, an

TABLE 4

ANTIMICROBIAL ACTIVITY (LOG REDUCTIONS) OF FATTY ACID MONOESTERS, ORGANIC ACIDS, ANIONIC AND NONIONIC SURFACTANT

| COMPOSITION | WT. % | S. AUREUS 2 MIN. | S. AUREUS 10 MIN. | E. COLI 2 MIN. | E. COLI 10 MIN. |
|---|---|---|---|---|---|
| GLYCEROL MONOLAURATE | 0.10 | >6.11 | >6.11 | >5.91 | >5.91 |
| LACTIC ACID | 0.10 | | | | |
| DOSS | 0.50 | | | | |
| PLURONIC F-68 | 0.50 | | | | |
| WATER | 98.80 | | | | |
| GLYCEROL MONOLAURATE | 0.10 | >6.11 | >6.11 | >5.91 | >5.91 |
| SUCCINIC ACID | 0.10 | | | | |
| DOSS | 0.50 | | | | |
| PLURONIC F-68 | 0.50 | | | | |
| WATER | 98.80 | | | | |
| GLYCEROL MONOLAURATE | 0.10 | >6.11 | >6.11 | >5.91 | >5.91 |
| CIMC ACID | 0.10 | | | | |
| DOSS | 0.50 | | | | |
| PLURONIC F-68 | 0.50 | | | | |
| WATER | 98.80 | | | | |
| GLYCEROL MONOLAURATE | 0.10 | >6.34 | >6.34 | >6.15 | >6.15 |
| ACETIC ACID | 0.10 | | | | |
| DOSS | 0.50 | | | | |
| PLURONIC F-68 | 0.50 | | | | |
| WATER | 98.80 | | | | |
| GLYCEROL MONOLAURATE | 0.10 | >6.11 | >6.11 | >5.91 | >5.91 |
| ASCORBIC ACID | 0.10 | | | | |
| DOSS | 0.50 | | | | |
| PLURONIC F-68 | 0.50 | | | | |
| WATER | 98.80 | | | | |
| GLYCEROL MONOLAURATE | 0.10 | >6.15 | >6.15 | >6.27 | >6.27 |
| DL MALIC ACID | 0.10 | | | | |
| DOSS | 0.50 | | | | |
| PLURONIC F-68 | 0.50 | | | | |
| WATER | 98.80 | | | | |
| GLYCEROL MONOLAURATE | 0.5 | >6.32 | >6.32 | >6.15 | >6.15 |
| SPORIX | 1.0 | | | | |
| DOSS | 0.25 | | | | |
| WATER | 98.25 | | | | |
| GLYCEROL MONOLAURATE | 0.10 | >6.15 | >6.15 | >6.27 | >6.27 |
| DL MANDELIC ACID | 0.10 | | | | |
| DOSS | 0.50 | | | | |
| PLURONIC F-68 | 0.50 | | | | |
| WATER | 98.80 | | | | |

DOSS-dioctyl sodium gulfosuccinate (50 wt. % in ethanol)

In sum, the dam listed in Tables 1–4 demonstrate that the three components contained in the composition of the present invention have effective antimicrobial activity when used together but none of the components when used alone or when combined with only one other component provided the desired antimicrobial activity. The antimicrobial activity of the present three component combination was unexpected and not predicted by the reported antimicrobial activity of the individual components. Example 2—Process Plant Testing for Spoilage The capability of the present invention to increase the shelf-life of processed poultry is demonstrated in this example. The data listed in Table 5 indicate that compositions of the present invention extend the shelf-life of processed poultry for at least an additional 4–7 days compared to poultry treated with a composition containing 20 ppm chlorine.

In this example, poultry carcasses (commercial strain broiler chicks innoculated via drinking water with $10^{6-7}$ colony forming units/ml Salmonella typhimurium, ATCC 14028, on days 2, 7, 14 and 21 and then processed at six weeks of age) were treated with six different solutions at about 0° C. for about sixty minutes and then refrigerated at about 4° C. The bacterial counts of the 4° C. carcasses were then measured over a period of time. When the bacterial counts of a standard whole carcass rinse were greater than $10^7$ (log 7.0) colony forming units/ml the carcasses were determined to be spoiled. Briefly, a poultry carcass was placed into a sterile bag filled with sterile water (100 ml). The bag was sealed and the bagged carcass was vigorously shaken for about one minute. After shaking, one corner of the bag was aseptically cut and a sample (80 ml) was removed and added to a sterile rinse bottle. Letheen broth (5-strength, 20 ml) was immediately added to the rinse bottle, the bottle was sealed, and the resulting mixture was shaken about twenty-five times. The mixture was kept cold (about 0° C.) until it was plated on both E. coli Count PETRIFILM and Aerobic Count PETRIFILM culture plates (3M, St. Paul, Minn.) in order to determine colony forming units/ml. Compositions of the present invention unexpectedly extended the shelf-life of the carcasses compared to carcasses washed with a sodium hypochlorite solution (20 ppm active chlorine) commonly used in poultry processing plants.

TABLE 5

EFFICACY OF COMPOSITIONS IN EXTENDING
THE SHELF-LIFE OF FRESHLY SLAUGHTERED
POULTRY CARCASSES

| COMPOSITION (DILUTION) | DAY 0 | DAY 17 | DAY 21 | DAY 23 |
|---|---|---|---|---|
| FORMULA 1 (32:1) | 1.82 | 5.67 | 7.80 | — |
| FORMULA 2 (32:1) | 2.37 | 5.00 | 7.70 | — |
| FORMULA 3 (32:1) | 2.22 | 6.49 | — | — |
| FORMULA 4 (32:1) | 2.20 | 2.42 | 6.85 | 6.17 |
| FORMULA 4 (64:1) | 2.91 | 2.19 | — | 4.63 |
| CHLORINE (20 PPM) | 3.92 | 7.28 | — | — | sample contained about one thousand salmonella cells. The inoculated samples were then treated with disinfectant compositions having formulas listed in Table 6. The samples were treated with the listed compositions for sixty minutes at 0° C. and for two minutes at 50° C. To determine the reduction of loose salmonella cells, the sample was shaken for one minute with buffered phosphate diluent (20 ml) and a sample (one ml) was then removed. To determine the reduction of attached salmonella cells, the rinsed skin was removed from the buffer above, was then blended in a commercial stomacher for two minutes with fresh water (20 ml) and a sample (one ml) was removed. The loose cell samples and attached cell samples were plated out on tryptic soy agar and colony counts were determined. Log reduction of cells was determined using the formula: ($\log_{10}$ colony

| | COMPOSITION DATA | | | |
|---|---|---|---|---|
| COMPONENTS (WT. %) | FORMULA 1 | FORMULA 2 | FORMULA 3 | FORMULA 4 |
| GLYCERYL MONOLAURATE | 1.0 | 1.0 | 1.0 | 1.0 |
| PROPYLENE GLYCOL MONOCAPRATE | 2.5 | 2.5 | 2.5 | 2.5 |
| PROPYLENE GLYCOL MONOCAPRYLATE | 2.5 | 2.5 | 2.5 | 2.5 |
| TARTARIC ACID | 6.0 | — | 6.0 | — |
| LACTIC ACID | — | 6.0 | — | 6.0 |
| PLURONIC F-68 | 10.0 | 5.0 | 5.0 | 10.0 |
| DIOCTYL SODIUM SULFOSUCCINATE (50 %) | 10.0 | 10.0 | 10.0 | 10.0 |
| PROPYLENE GLYCOL | 15.0 | 73.0 | 73.0 | 15.0 |
| WATER | 53.0 | — | — | 53.0 |

Example 3—Salmonella Testing

This example demonstrates that a three component composition containing one or more fatty acid monoesters, an acid or chelating agent, an anionic surfactant and a nonionic surfactant provides effective antimicrobial activity against *Salmonella typhimurium* when the components of the composition are used at concentrations which do not change or alter the taste, texture, color, odor or appearance of the processed poultry. The data listed in Table 6 also demonstrate that the compositions had effective antimicrobial activity when used at about 0° C. for sixty minutes and at about 50° C. for two minutes. These temperatures and times correspond to the temperatures and times used in processing chill tanks and scald tanks, respectively.

In this example, fresh poultry breast skin obtained from a local processing plant was cut into circular pieces (10 cm in diameter) each piece was individually packaged and the packaged pieces were sterilized by irradiation using known procedures. After irradiation, the poultry skin samples were artificially inoculated by contacting the samples with *Salmonella typhimurium* for about ten minutes. Each inoculated forming units inoculated skin treated only with water) - ($\log_{10}$ colony forming units inoculated skin treated with disinfectant composition). Untreated control samples for loose and attached cells were obtained following the above procedures.

The listed data indicate that two component compositions, Formulas 5–8, were generally less effective than the three component compositions, Formulas 9–22, at reducing the number of both loose and attached salmonella cells (log reduction of the number of loose and attached cells of the treated skin compared to the number of loose and attached cells of the untreated skin).

In addition, the three component compositions of Formulas 9–22 were generally as effective as or more effective than acetic acid, trisodium phosphate or sodium hypochlorite solutions at reducing the numbers of loose and attached salmonella cells. The antimicrobial effect of these solutions are listed in Table 7. These solutions caused undesired discoloration of the poultry skin.

TABLE 6

ANTIMICROBIAL EFFECT (LOG REDUCTIONS) AGAINST LOOSE
AND ATTACHED SALMONELLA TYPHIMURIUM

| | | 0° C. | | 50° C. | |
|---|---|---|---|---|---|
| COMPOSITION | DILUTION | LOOSE | ATTACHED | LOOSE | ATTACHED |
| FORMULA 5 | 16:1 | 0.62 | 0.86 | 0.80 | 0.30 |
| | 32:1 | 0.27 | 0.55 | 0.60 | 0.48 |

TABLE 6-continued

ANTIMICROBIAL EFFECT (LOG REDUCTIONS) AGAINST LOOSE
AND ATTACHED SALMONELLA TYPHIMURIUM

| | | 0° C. | | 50° C. | |
|---|---|---|---|---|---|
| COMPOSITION | DILUTION | LOOSE | ATTACHED | LOOSE | ATTACHED |
| FORMULA 6 | 16:1 | 0.65 | 1.58 | 0.63 | 0.01 |
| | 32:1 | 0.36 | 0.76 | 0.52 | 0.80 |
| FORMULA 7 | 16:1 | 0.45 | 0.79 | 0.92 | 0.59 |
| | 32:1 | 0.39 | 0.54 | 0.52 | 0.45 |
| FORMULA 8 | 16:1 | 0.67 | 0.88 | 0.67 | 0.61 |
| | 32:1 | 0.36 | 0.60 | 0.60 | 0.60 |
| FORMULA 9 | 32:1 | — | 1.00 | — | 0.93 |
| | 128:1 | | 1.34 | | 0.36 |
| FORMULA 10 | 16:1 | 1.15 | 1.15 | 0.67 | 1.16 |
| | 32:1 | 0.93 | 0.66 | 1.27 | 1.06 |
| FORMULA 11 | 16:1 | 1.05 | 1.22 | 0.74 | 1.18 |
| | 32:1 | 1.22 | 0.69 | 1.27 | 0.97 |
| FORMULA 12 | 16:1 | 0.89 | 1.19 | 0.60 | 1.05 |
| | 32:1 | 1.03 | 0.66 | 1.02 | 0.85 |
| FORMULA 13 | 16:1 | 1.03 | 1.18 | 0.51 | 1.17 |
| | 32:1 | 0.75 | 0.47 | 1.19 | 0.92 |
| FORMULA 14 | 32:1 | — | 1.45 | — | 0.61 |
| | 128:1 | | 0.30 | | 0.20 |
| FORMULA 15 | 32:1 | — | 0.92 | — | 0.67 |
| | 128:1 | | 0.41 | | 0.06 |
| FORMULA 16 | 32:1 | — | 1.47 | — | 0.93 |
| | 128:1 | | 0.43 | | 0.18 |
| FORMULA 17 | 128:1 | 0.37 | 0.48 | 1.01 | 0.78 |
| | 32:1 | 2.13 | 1.21 | 1.13 | 1.68 |
| FORMULA 18 | 128:1 | −0.13 | 0.04 | 0.40 | 0.16 |
| | 32:1 | 0.73 | 0.53 | 0.94 | 1.62 |
| FORMULA 19 | 128:1 | −0.21 | 0.23 | 0.44 | 1.04 |
| | 32:1 | 2.24 | 0.81 | 1.19 | 1.64 |
| FORMULA 20 | 128:1 | 0.34 | 0.63 | 0.82 | 0.44 |
| | 32:1 | 0.96 | 0.61 | 0.98 | 1.68 |
| FORMULA 21 | 128:1 | −0.08 | 0.08 | 0.77 | 0.80 |
| | 32:1 | 2.55 | 1.98 | 1.14 | 1.17 |
| FORMULA 22 | 128:1 | −0.08 | 1.19 | 0.51 | 1.37 |
| | 32:1 | 2.55 | 1.83 | 1.36 | 1.10 |

COMPOSITION DATA

| | FORMULAS | | | | | | | | | | | |
|---|---|---|---|---|---|---|---|---|---|---|---|---|
| COMPONENTS | 5 | 6 | 7 | 8 | 9 | 10 | 11 | 12 | 13 | 14 | 15 | 16 |
| GLYCEROL MONOLAURATE | — | — | — | — | — | 1.0 | 1.0 | 1.0 | 1.0 | 1.5 | 1.5 | 1.0 |
| PROP. GLYCOL MONOCAPRYLATE | — | — | — | — | 10.0 | 2.5 | 2.5 | 2.5 | 2.5 | 5.0 | 5.0 | 10.0 |
| PROP. GLYCOL MONOCAPRATE | — | — | — | — | 10.0 | 2.5 | 2.5 | 2.5 | 2.5 | 5.0 | 5.0 | 10.0 |
| LACTIC ACID | 6.0 | 6.0 | — | — | 4.0 | 6.0 | — | 6.0 | — | — | — | 10.0 |
| TARTARIC ACID | — | — | 6.0 | 6.0 | — | — | 6.0 | — | 6.0 | — | — | — |
| MANDELIC ACID | — | — | — | — | — | — | — | — | — | 4.0 | — | — |
| SPORIX | — | — | — | — | — | — | — | — | — | — | 4.0 | — |
| PLURONIC F-68 | — | — | — | — | 5.0 | 10.0 | 10.0 | 5.0 | 5.0 | 10.0 | 10.0 | 5.0 |
| PROPYLENE GLYCOL | 15.0 | 84.0 | 15.0 | 84.0 | 61.0 | 15.0 | 15.0 | 73.0 | 73.0 | 15.0 | 15.0 | 54.0 |
| DIOCTYL SODIUM SULFOSUCCINATE (50%) | 10.0 | 10.0 | 10.0 | 10.0 | 10.0 | 10.0 | 10.0 | 10.0 | 10.0 | 10.0 | 10.0 | 10.0 |
| WATER | 69.0 | — | 69.0 | — | — | 53.0 | 53.0 | — | — | 49.5 | 49.5 | — |

| | FORMULAS | | | | | |
|---|---|---|---|---|---|---|
| COMPONENTS | 17 | 18 | 19 | 20 | 21 | 22 |

-continued

| COMPOSITION DATA | | | | | | |
|---|---|---|---|---|---|---|
| PROPYLENE GLYCOL MONOCAPRATE | — | 20.0 | — | 20.0 | — | — |
| PROPYLENE GLYCOL MONOCAPRYLATE | 20.0 | — | 20.0 | — | 20.0 | 20.0 |
| ACETIC ACID | — | — | — | — | 2.0 | 4.0 |
| MANDELIC ACID | — | — | 4.0 | 4.0 | — | — |
| LACTIC ACID | 4.0 | 4.0 | — | — | 2.0 | 4.0 |
| PLURONIC F-68 | 5.0 | 5.0 | 5.0 | 5.0 | 10.0 | 10.0 |
| DIOCTYL SODIUM SULFOSUCCINATE (50%) | 10.0 | 10.0 | 10.0 | 10.0 | 2.0 | 2.0 |
| PROPYLENE GLYCOL | 61.0 | 61.0 | 61.0 | 61.0 | 64.0 | 60.0 |

TABLE 7

ANTIMICROBIAL EFFECT (LOG REDUCTION) OF ACETIC ACID, SODIUM HYPOCHLORITE AND TRISODIUM PHOSPHATE

| COMPO- SITION | 0° C. | | 50° C. | |
|---|---|---|---|---|
| | LOOSE | ATTACHED | LOOSE | ATTACHED |
| CHLORINE (20 PPM) | 0.06 | 0.22 | 0.50 | 0.79 |
| CHLORINE (400 PPM) | 2.27 | 1.28 | 0.74 | 0.90 |
| CHLORINE (800 PPM) | ≧2.52 | 1.87 | 1.71 | 1.33 |
| 5% ACETIC ACID | ≧2.52 | <0 | 1.69 | 2.00 |
| 8% TRI- SODIUM PHOS- PHATE | 1.65 | 1.82 | 1.52 | 1.16 |

Example 4—Process Plant Testing for Salmonella

This example demonstrates that the compositions of the present invention are more effective against Salmonella spp. than commonly used chlorinated solutions. In this example, freshly slaughtered poultry carcasses were disinfected for sixty minutes in an ice cooled chill tank with either a conventional chlorine solution (20 ppm) or with four different compositions, Formulas 1–4 of Example 2, of the present invention. After treatment, each poultry carcass was then rinsed according to the procedure set out in Example 2.

A sample of the rinse water (10.0 ml) was diluted with selenite cystine media (90.0 ml, DIFCO Laboratories, Detroit, Mich.) and incubated at 37° C. for twenty-four hours to enrich for salmonella. After enrichment, samples were plated on xylose lysine desoxycholate and Bacto hektoen enteric agar at 37° C. for twenty-four hours and confirmation of salmonella was confirmed by stab slants on triple sugar iron and lysine sugar agar following known procedures. The presence of salmonella indicated a positive carcass or the absence of salmonella indicated a negative carcass.

The results listed in Table 8 indicate that the four compositions of the present invention were significantly better at reducing Salmonella spp. contamination of the poultry carcasses compared to poultry treated with a sodium hypochlorite solution.

TABLE 8

EFFICACY OF COMPOSITIONS AGAINST SALMONELLA ON FRESHLY SLAUGHTERED POULTRY CARCASSES

| COMPOSITION | DILUTION | # SAMPLED CARCASSES | # POSITIVE CARCASSES | PERCENT REDUCTION |
|---|---|---|---|---|
| FORMULA 1 | 32:1 | 20 | 1 | 95 |
| FORMULA 2 | 32:1 | 20 | 4 | 80 |
| FORMULA 3 | 32:1 | 20 | 0 | 100 |
| FORMULA 4 | 32:1 | 20 | 9 | 55 |
| CHLORINE (20 PPM) | — | 20 | 13 | 35 |

We claim:

1. A disinfectant composition for use on foods consisting essentially of effective amounts of a) a fatty acid monoester selected from the group consisting of glycerol and propylene glycol monoesters of caprylic, capric and lauric acid;

b) an acid or chelating agent selected from the group consisting of lactic acid, tartaric acid, adipic acid, succinic acid, citric acid, ascorbic acid, malic acid, mandelic acid, acetic acid, sorbic acid, sodium acid pyrophosphate, acidic sodium hexametaphosphate, and ethylenediaminetetraacetic acid and salts thereof;

c) a food grade anionic surfactant; and d) a vehicle;

wherein the amounts of a), b) or c) in the composition either taken alone or as a combination of a) and b), a) and c), or b) and c) do not have effective antimicrobial activity and wherein the amounts of a), b) and c) in the composition taken together have effective antimicrobial activity, wherein said effective antimicrobial activity is activity against both gram-negative and gram-positive bacteria by killing the bacteria within about two minutes of contact with the composition to provide a log reduction of greater than about 5.91 when contacted with an inoculum having an initial bacterial concentration of about $10^6$ to $10^8$ cells per ml.

2. The disinfectant composition of claim 1 wherein the vehicle is selected from the group consisting of water, propylene glycol, polyethylene glycol, and mixtures thereof.

3. The disinfectant composition of claim 1 wherein the vehicle is water.

4. The disinfectant composition of claim 1 wherein the food grade anionic surfactant is dioctyl sodium sulfosuccinate or sodium lauryl sulfate.

5. The disinfectant composition of claim 1 wherein the acid is selected from the group consisting of acetic, lactic, tartaric, and mandelic acid.

6. The disinfectant composition of claim 1 wherein the fatty acid monoester is a glycerol monoester of lauric acid.

7. A disinfectant composition for use on foods consisting essentially of a) about 0.005–1.0 wt. % of a fatty acid monoester selected from the group consisting of glycerol and propylene glycol monoesters of caprylic, capric and lauric acid;

b) about 0.01–0.5 wt. % of an acid or chelating agent selected from the group consisting of lactic acid, tartaric acid, adipic acid, succinic acid, citric acid, ascorbic acid, malic acid, mandelic acid, acetic acid, sorbic acid, sodium acid pyrophosphate, acidic sodium hexametaphosphate, and ethylenediaminetetraacetic acid and salts thereof;

c) about 0.01–0.5 wt. % of a food grade anionic surfactant; and d) the remainder water;

wherein the amounts of a), b) or c) in the composition taken alone or as a combination of a) and b), a) and c), or b) and c) do not have effective antimicrobial activity and wherein the amounts of a), b) and c) in the composition taken together have effective antimicrobial activity, wherein said effective antimicrobial activity is activity against both gram-negative and gram-positive bacteria by killing the bacteria within about two minutes of contact with the composition to provide a log reduction of greater than about 5.91 when contacted with an inoculum having an initial bacterial concentration of about $10^6$ to $10^8$ cells per ml.

8. A disinfectant composition for use on foods consisting essentially of effective amounts of a) a fatty acid monoester selected from the group consisting of glycerol and propylene glycol monoesters of caprylic, capric and lauric acid;

b) an acid or chelating agent selected from the group consisting of lactic acid, tartaric acid, adipic acid, succinic acid, citric acid, ascorbic acid, malic acid, mandelic acid, acetic acid, sorbic acid, sodium acid pyrophosphate, acidic sodium hexametaphosphate, and ethylenediaminetetraacetic acid and salts thereof;

c) a food grade anionic surfactant;

d) a nonionic surfactant; and e) a vehicle;

wherein the amounts of a), b) or c) in the composition either taken alone or as a combination of a) and b), a) and c), or b) and c) do not have effective antimicrobial activity and wherein the amounts of a), b) and c) in the composition taken together have effective antimicrobial activity, wherein said effective antimicrobial activity is activity against both gram-negative and gram-positive bacteria by killing the bacteria within about two minutes of contact with the composition to provide a log reduction of greater than about 5.91 when contacted with an inoculum having an initial bacterial concentration of about $10^6$ to $10^8$ cells per ml.

9. The disinfectant composition of claim 8 wherein the nonionic surfactant is a polyoxyethylene/polyoxypropylene block copolymer.

* * * * *